United States Patent [19]
Vaphiades et al.

[11] Patent Number: 5,920,374
[45] Date of Patent: Jul. 6, 1999

[54] COMPUTERIZED SCREENING DEVICE UTILIZING THE PULFRICH EFFECT

[75] Inventors: Michael S. Vaphiades; Lawrence M. Merin, both of Little Rock, Ark.

[73] Assignee: Board of Trustees of the University of Arkansas, Little Rock, Ark.

[21] Appl. No.: 09/047,019

[22] Filed: Mar. 24, 1998

[51] Int. Cl.$^6$ ........................................................ A61B 3/02
[52] U.S. Cl. ............................................ 351/237; 600/558
[58] Field of Search ................................. 351/222, 223, 351/233, 237, 240, 246; 359/462, 466, 359/475; 600/558

[56] References Cited

U.S. PATENT DOCUMENTS

| | | | |
|---|---|---|---|
| 4,893,898 | 1/1990 | Beard | 350/132 |
| 5,099,858 | 3/1992 | Hofeldt | 128/745 |
| 5,347,330 | 9/1994 | Hofeldt | 351/223 |
| 5,355,895 | 10/1994 | Hay | 600/558 |
| 5,365,370 | 11/1994 | Hudgins | 359/464 |
| 5,564,000 | 10/1996 | Halpern | 395/152 |

OTHER PUBLICATIONS

Vaphiades, "The Pulfrich Effect and its Relationship to Retinal Illumination," Journal of Neuro–Ophthalmology, 1997, pp. 240–242.

*Primary Examiner*—George Manuel
*Attorney, Agent, or Firm*—Ray F. Cox, Jr.

[57] ABSTRACT

A method and device which utilizes the Pulfrich stereo-illusion effect to screen for anterior visual system disease. The Pulfrich stereo-illusion effect occurs when viewing a pendulum moving perpendicular to the line of sight. If one eye is affected by anterior visual system disease, the pendulum appears to move in an ellipse—clockwise if the left eye is affected, counter-clockwise if the right eye if affected. A computer has software to generate an image of a "pendulum" bob. The patient views this image through a set of "virtual reality" goggles connected to the computer. The computer generates left and right images for presentation to each eye that mimic the varying perspective of real three dimensional objects viewed directly by the human eyes. The computer also generates a set of "neutral density" filters for each eye so that the degree of impairment in an eye may be quantified.

9 Claims, 1 Drawing Sheet

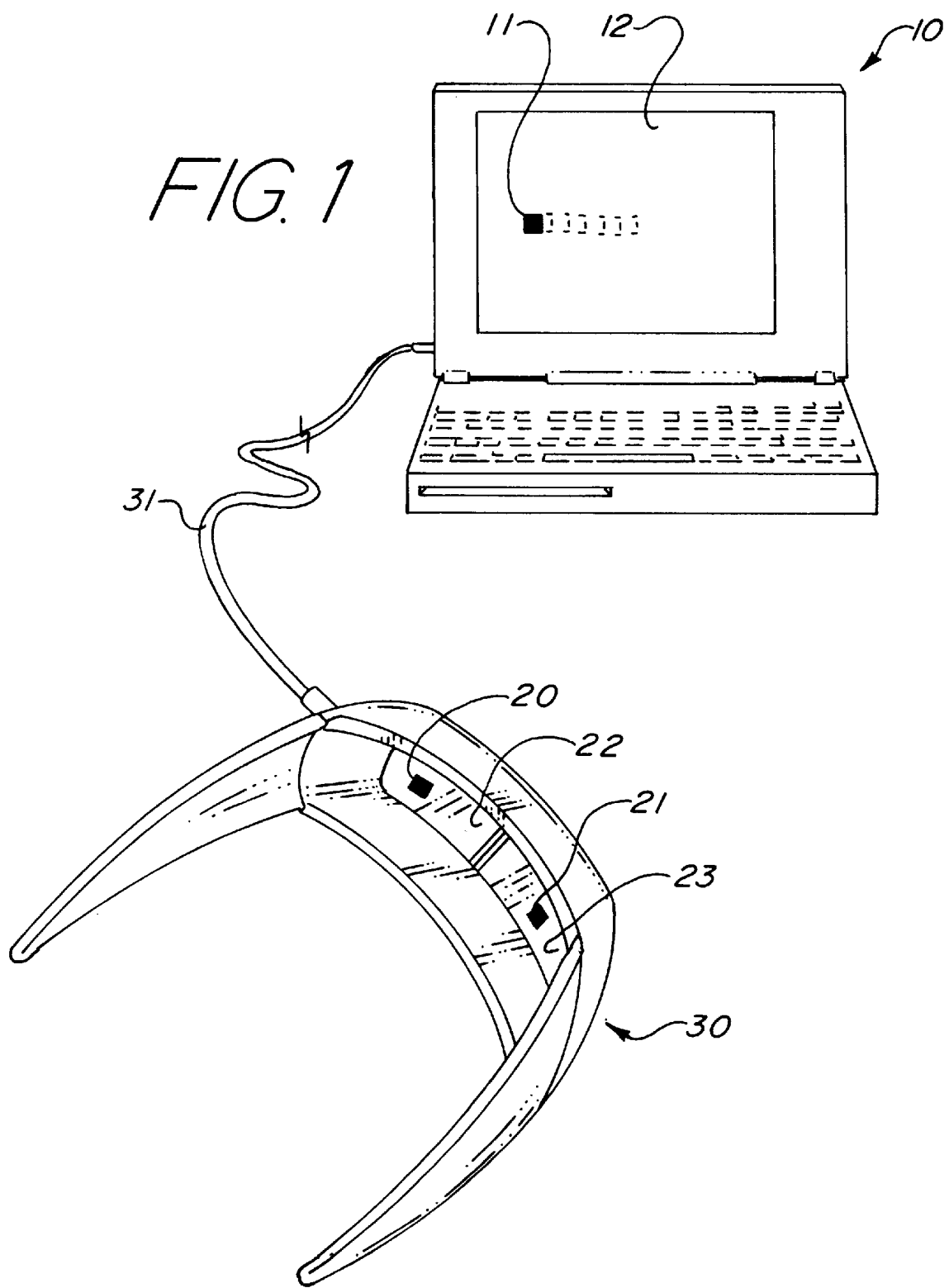

COMPUTERIZED SCREENING DEVICE UTILIZING THE PULFRICH EFFECT

BACKGROUND OF THE INVENTION

The present invention relates to devices useful for diagnosing visual system diseases, and in particular to a computerized device for screening anterior visual system diseases utilizing the Pulfrich effect.

The Pulfrich effect is a stereo-illusion effect which occurs in patients with a degree of impairment in one eye. A pendulum moving perpendicular to the line of sight is presented to the patient. Normally the pendulum appears to the patient to move linearly. However, if one eye is affected by anterior visual system disease, a stereo-illusion causes the pendulum to appear to move in an ellipse. The elliptical motion of the pendulum is clockwise if the left eye is affected and counter-clockwise if the right eye is affected.

The degree of impairment may be assessed by utilizing neutral density filters of varying density in front of the less impaired eye. When filters of appropriate density are chosen, the stereo-illusion effect disappears.

The Pulfrich effect has been employed to test for anterior visual system disease utilizing actual pendulums. For example, the prior art discloses the use of bulky mechanical pendulums, such as disclosed in U.S. Pat. No. 5,099,858 to Hofeldt. Hofeldt '858 discloses a device for diagnosing ocular and optic nerve disease utilizing the Pulfrich effect comprising an enclosure with two eyepieces, a pendulum bob and a reference point for the bob. Hofeldt '858 also provides means for varying the light perceived through each of the eyepieces.

U.S. Pat. No. 5,347,330 also issued to Hofeldt discloses the use of an audio/visual recording showing a figure moving in a pendulum-like fashion to produce the Pulfrich effect. In order to use this device, the person being tested views the audio/visual recording through a device which sequentially provides filters of varying density.

While the prior art discloses the use of the Pulfrich stereo-illusion effect to test for anterior visual system disease, the mechanisms suggested in the prior art are not suitable for many classes of patients, such as pre-verbal children or supine patients.

These and other limitations of the prior art are overcome by the present invention.

SUMMARY OF THE INVENTION

The invention is a method and device which utilizes the Pulfrich stereo-illusion effect to screen for anterior visual system disease. The Pulfrich stereo-illusion effect occurs when viewing a pendulum moving perpendicular to the line of sight. If one eye is affected by anterior visual system disease, the pendulum appears to move in an ellipse—clockwise if the left eye is affected, counter-clockwise if the right eye if affected.

The present invention comprises a computer with software to generate a "pendulum" dot. The patient views this image through a set of "virtual reality" goggles connected to the computer. "Virtual reality" is a term employed to describe computer generated images that give the illusion of full three dimensional reality. The computer generates left and right images for presentation to each eye that mimic the varying perspective of real three dimensional objects viewed directly by the human eyes.

The computer also generates a set of "neutral density" filters for each eye so that the degree of impairment in an eye may be quantified.

Additional software may be included with the device to allow for the testing of color vision, visual acuity, contrast sensitivity, visual field, and the like.

A major advantage for this invention over the prior art is that the technique may be employed with a wide range of patients who might not be easily tested using the prior art methods which employ bulky pendulums or video displays—for example, pre-verbal children or supine patients. With pre-verbal children, symbols may be used in place of words. The present invention would also be beneficial in applications where trained ophthalmologists are not available, such as rural areas, outer space (NASA) applications, or military applications. The present invention offers exceptional advantages when testing supine patients; for example, in nursing homes, or in emergency rooms. In the later situation, trauma checking is facilitated. Other examples of the utility of the present invention include the testing of patients suffering from arthritis who may often be unable to physically accommodate the demands of standard testing devices.

It is therefore an object of the present invention to employ a computer to generate a Pulfrich effect "pendulum" to screen patients for anterior visual system disease.

It is a further object of the present invention to employ a computer to generate neutral density filters to assess the degree of visual impairment shown by the Pulfrich effect.

It is also an object of the present invention to provide for anterior visual system disease screening of supine and pre-verbal patients not readily testable using the prior art technology.

It is a still further object of the present invention to provide for the ability to combine a number of testing methodologies in a single software package; for example, visual acuity testing and the like.

These and other objects and advantages of the present invention will be seen from a consideration of the following detailed description of the preferred embodiments in conjunction with the appended drawings as described following.

BRIEF DESCRIPTION OF THE DRAWING

FIG. 1 is a perspective view of a computer and visual reality goggles as utilized in the practice of the present invention.

DETAILED DESCRIPTION OF THE PREFERRED EMBODIMENTS

The Pulfrich Stereo-illusion Effect occurs in patients with monocular anterior visual system disease when viewing a pendulum situated perpendicular to their line of vision. The effect consists of a counter-clockwise appearing ellipse if the right eye is affected, or a clockwise effect if the left eye is affected.

The present invention is a method and device which uses the Pulfrich Effect to screen for anterior visual system disease (optic neuropathy or pan-retinal disease) both in the clinic and at the bedside for non-ambulatory patients.

The present invention is described with reference to FIG. 1. In the preferred embodiment, a small notebook-type computer 10 is provided with software to generate a dot 11 that moves back and forth in a pendulum-like fashion. The preparation of software to generate such a dot is well within the capabilities of one skilled in the art. The dot 11 may be displayed on a screen 12 of the computer 10 as shown in FIG. 1. This display is solely for the benefit of the person conducting the screening test; the patient does not view the image of the dot 11 on the screen 12. The dot 11 in the preferred embodiment is a simple solid square shape. While other shapes may be desirable in certain applications, the simpler shapes are preferred to provide a sharp easily visualized target for the patient. More complex shapes are less likely to provide a clear stereo-illusion effect and thus are of less value in quantifying the degree of visual impairment in the patient.

In addition to generating the dot 11 for display on the screen 12, the software in the computer 10 generates a virtual left image 20 and a virtual right image 21 of the pendulum dot 11. The virtual images 20, 21 are transmitted from the computer 10 to virtual reality goggles 30 by cable 31 or by other transmission means known in the art, such as wireless infrared transmission.

The left virtual image 20 is presented to a left display 22 and the right virtual image 21 is presented to a right display 23. The displays 22, 23 may be of any of various types of display apparatus, such as miniature cathode ray tubes, liquid crystal displays or any other type of apparatus capable of presenting a moving computer generated visual image directly to each eye of the patient.

The software generates virtual images 20, 21 so as to mimic the perspective effect of an actual dot moving perpendicular to the line of sight of the virtual reality goggles 30 at an assumed distance from the patient. For an image as simple as a dot or similar simple geometric shape, the calculation of the left and right virtual images 20, 21 is within the capabilities of one skilled in the art. For a dot which simulates the movement of a pendulum bob perpendicular to the line of sight of the viewer, the images are simply displaced from the center of the display by an amount equivalent to the perceived image of a dot moving perpendicular to the line of sight at a fixed distance. When viewing the two virtual images 20, 21 simultaneously, the patient is presented with the illusion of viewing an actual moving pendulum in three dimensional space; i.e., a virtual pendulum.

If the patient has no anterior visual system disease, the virtual pendulum derived from the virtual images 20, 21 will appear to move in a straight line from left to right and back. If the patient has some degree of anterior visual system disease, the "virtual pendulum" will appear to describe an ellipse.

To assess quantitatively the degree of visual system impairment, the software generates a neutral density filter, which diminishes the brightness of the virtual image presented to the unimpaired eye until the stereo-illusion ceases. At this point the unimpaired eye has been presented with an image equivalent to that perceived by the impaired eye. By this method, the degree of impairment may be quantified.

The software will permit adjustment of dot size, speed of movement in addition to the introduction of neutral density to verify data. It will also allow the clinician to independently test each eye of the patient.

The presently available technology for assessing a patient utilizing the Pulfrich effect consists of a bulky pendulum or of a video display of a figure moving back and forth on a television screen. The complex target figure used in the video method obscures the phenomenon. Furthermore, for supine patients the test cannot be accomplished by either method since each requires the patient to view a moving image from an upright posture. The use of virtual reality goggles, however, allows supine patients to be tested.

Additional software may be included to allow for the testing of color vision, visual acuity, contrast sensitivity, visual fields, and the like.

The present invention is portable, provides a cleaner target figure, and thus is a more reliable method for measuring the Pulfrich effect. The introduction of computer-generated neutral density for each eye permits the neutralization of the effect, and thus increases the reliability of test date. The device allows the clinician an easy and accurate way of determining anterior visual system disease.

The present invention has been described with reference to certain preferred and alternative embodiments which are intended to be exemplary only and not limiting to the full scope of the present invention as set forth in the appended claims.

What is claimed is:

1. A device for testing for anterior visual system disease using the Pulfrich stereo-illusion effect in a patient, comprising:

computer means for generating left and right virtual images of a virtual pendulum bob moving back and forth perpendicular to the light of sight of the patient;

virtual reality goggles having left and right display means for displaying said left and right virtual images respectively; and transmission means for transmitting said left and right virtual images from said computer means to said virtual reality goggles.

2. The device of claim 1 wherein said computer means further comprises means to vary the brightness of at least one of said virtual images.

3. The device of claim 2 wherein said computer means further comprises means to adjust the size of said virtual pendulum bob.

4. The device of claim 3 wherein said computer means further comprises means to vary the rate of movement of said virtual pendulum bob.

5. A method for testing for anterior visual system disease using the Pulfrich stereo illusion effect in a patient, comprising the steps of:

(a) generating left and right virtual images of a virtual pendulum bob moving back and forth perpendicular to the light of sight of the patient;

(b) placing on the patient virtual reality goggles having left and right display means for displaying said left and right virtual images respectively;

(c) displaying said left and right virtual images on said virtual reality goggles;

(d) determining whether the patient observes an elliptical motion of said virtual pendulum bob; and (e) varying the brightness of at least one of said virtual images until the patient observes no elliptical movement of said virtual pendulum bob.

6. The method of claim 5, further comprising the step of testing the patient for visual accuity.

7. The method of claim 5, further comprising the step of testing the patient for color vision.

8. The method of claim 5, further comprising the step of testing the patient for contrast sensitivity.

9. The method of claim 5, further comprising the step of testing the patient for visual field.

* * * * *